(12) United States Patent
Eum et al.

(10) Patent No.: US 9,960,363 B2
(45) Date of Patent: May 1, 2018

(54) ORGANIC ELECTROLUMINESCENT ELEMENT

(71) Applicant: DOOSAN CORPORATION, Seoul (KR)

(72) Inventors: Min-Sik Eum, Seoul (KR); Ho-Cheol Park, Yongin-si (KR); Chang Jun Lee, Suwon-si (KR); Tae Hyung Kim, Yongin-si (KR); Jiyi Kim, Yongin-si (KR); Youngmi Beak, Yongin-si (KR)

(73) Assignee: DOOSAN CORPORATION, Seoul (KR)

( * ) Notice: Subject to any disclaimer, the term of this patent is extended or adjusted under 35 U.S.C. 154(b) by 0 days. days.

(21) Appl. No.: 15/538,781

(22) PCT Filed: Dec. 21, 2015

(86) PCT No.: PCT/KR2015/014021
§ 371 (c)(1),
(2) Date: Jun. 22, 2017

(87) PCT Pub. No.: WO2016/105050
PCT Pub. Date: Jun. 30, 2016

(65) Prior Publication Data
US 2018/0013072 A1  Jan. 11, 2018

(30) Foreign Application Priority Data

Dec. 24, 2014 (KR) .................. 10-2014-0188953
Dec. 10, 2015 (KR) .................. 10-2015-0176096

(51) Int. Cl.
*H01L 51/00* (2006.01)
*C07D 251/24* (2006.01)
(Continued)

(52) U.S. Cl.
CPC ........ *H01L 51/0067* (2013.01); *C07D 251/24* (2013.01); *H01L 51/0052* (2013.01);
(Continued)

(58) Field of Classification Search
CPC ............ H01L 51/0052; H01L 51/5004; H01L 51/0054; H01L 51/0055; H01L 51/5016;
(Continued)

(56) References Cited

U.S. PATENT DOCUMENTS 8,679,647 B2   3/2014  Pflumm et al.
9,209,406 B2  12/2015  Mizutani et al.
(Continued)

FOREIGN PATENT DOCUMENTS

CN   102372665 A   3/2012
JP   2014-125449 A   7/2014
(Continued)

OTHER PUBLICATIONS

International Searching Authority, International Search Report of PCT/KR2015/014021, dated Apr. 15, 2016. [PCT/ISA/210].
(Continued)

*Primary Examiner* — (Vikki) Hoa B Trinh
(74) *Attorney, Agent, or Firm* — Sughrue Mion, PLLC

(57) ABSTRACT

The present invention provides an organic electroluminescent element which comprises: an anode; a cathode; and an organic layer interposed between the anode and the cathodes, wherein the organic layer comprises one or more types of layer from the group consisting of a hole-injection layer, hole-transport layer, light-emitting layer, lifetime enhancement layer, electron-transport layer, and electron-injection layer.

16 Claims, 1 Drawing Sheet

(51) Int. Cl.
*H01L 51/50* (2006.01)
*H01L 51/52* (2006.01)

(52) U.S. Cl.
CPC ...... H01L 51/0054 (2013.01); H01L 51/0055 (2013.01); H01L 51/5004 (2013.01); *H01L 51/5016* (2013.01); *H01L 51/5072* (2013.01); *H01L 51/5092* (2013.01); *H01L 51/52* (2013.01); *H01L 2251/552* (2013.01)

(58) Field of Classification Search
CPC . H01L 51/5072; H01L 51/5092; H01L 51/52; H01L 51/0067
See application file for complete search history.

(56) References Cited

U.S. PATENT DOCUMENTS

| | | | |
|---|---|---|---|
| 9,266,851 | B2 | 2/2016 | Yoshida et al. |
| 9,624,193 | B2 | 4/2017 | Aihara et al. |
| 9,640,766 | B2 | 5/2017 | Jang et al. |
| 2009/0251049 | A1* | 10/2009 | Kim ............... C09K 11/06 313/504 |
| 2011/0095282 | A1 | 4/2011 | Pflumm et al. |
| 2012/0261650 | A1* | 10/2012 | MacDonald ......... C07D 233/61 257/40 |
| 2013/0082248 | A1* | 4/2013 | Groarke ............. C07F 15/0033 257/40 |
| 2014/0001456 | A1 | 1/2014 | Mizutani et al. |
| 2014/0073784 | A1 | 3/2014 | Mizutani et al. |
| 2014/0100367 | A1 | 4/2014 | Yoon et al. |
| 2015/0025239 | A1 | 1/2015 | Ahn et al. |
| 2017/0033294 | A1 | 2/2017 | Jang et al. |

FOREIGN PATENT DOCUMENTS

| | | |
|---|---|---|
| KR | 10-2011-0112186 A | 10/2011 |
| KR | 10-2012-0046778 A | 5/2012 |
| KR | 10-2012-0052231 A | 5/2012 |
| KR | 10-2012-0132815 A | 12/2012 |
| KR | 10-2013-0094903 A | 8/2013 |
| KR | 10-2014-0046541 A | 4/2014 |
| KR | 10-2014-0101661 A | 8/2014 |
| KR | 10-1542714 B1 | 8/2015 |
| KR | 10-2015-0115648 A | 10/2015 |
| KR | 10-1745799 B1 | 6/2017 |
| WO | 2015/152650 A1 | 10/2015 |

OTHER PUBLICATIONS

Korean Intellectual Property Office, Communication dated Nov. 21, 2016 in counterpart application No. 10-2015-0171639.
Korean Intellectual Property Office, Communication dated Jul. 31, 2017 in counterpart application No. 10-2017-0015045.

* cited by examiner

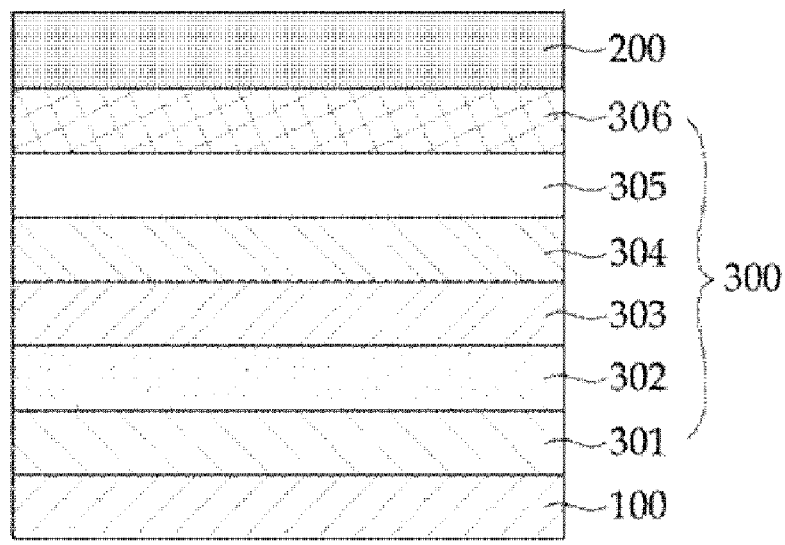

ORGANIC ELECTROLUMINESCENT ELEMENT

TECHNICAL FIELD

The present invention relates to an organic electroluminescent element comprising an organic layer.

BACKGROUND ART

Studies on an electroluminescent (EL) element have led to blue electroluminescence using a single crystal of anthracene in 1965, and then, an organic electroluminescent element of a bilayer structure consisting of a hole layer (NPB) and a light-emitting layer ($Alq_3$) was proposed by Tang in 1987. Since then, studies have been directed toward the implementation of high efficiency and long lifespan in electroluminescent elements, suggesting a multilayer structure comprising an organic layer responsible for hole injection or hole transport, an organic layer responsible for electron injection or electron transport, and an organic layer responsible for combining a hole and an electron to induce electroluminescence. The introduction of multilayer structures has improved performance of organic electroluminescent elements to a level of commercialization. As a result, starting from radio display products for automobiles in 1997, the application of organic electroluminescence elements has been expanded to mobile information display devices and TV displays.

Requirements of enlargement and high resolution for displays are accompanied by the problems of high efficiency and long lifespan in organic electroluminescence elements in high resolution displays. Particularly, the high resolution that is achieved by forming more pixels in the same area reduces a luminescent area of organic electroluminescent elements, incurring a decrease in lifespan. This is one of the most important technical problem to be solved for organic electroluminescent elements.

In an organic electroluminescent element, the application of a current or voltage across two opposite electrodes induces the injection of holes from the anode and electrons from the cathode into an organic layer. The injected holes and electrons recombine with each other to generate excitons which then return to the ground state, emitting light. According to kinds of electron spin of the excitons formed, the organic electroluminescent elements may be classified into fluorescent light-emitting elements in which decay of singlet excitons contributes to the production of light through spontaneous emission and phosphorescent light-emitting elements in which decay of triplet excitons contributes to the production of light through spontaneous emission.

Electron spin of excitons formed by the recombination of electrons and holes may either be in a singlet state or a triplet state at a ratio of 25% singlet state:75% triplet state. Fluorescent light-emitting elements in which light is emitted by singlet exciton, theoretically does not exceed 25% in internal quantum efficiency and 5% in external quantum efficiency, based on the formation rate of a singlet excitons. Phosphorescent light-emitting elements in which light is emitted by triplet exciton exhibits emission efficiency four times as high as that of fluorescent light-emitting elements.

Although phosphorescent light-emitting elements are higher in emission efficiency than fluorescent light-emitting elements, as described above, on a theoretical basis, a host that meets the color purity of deep blue and the high efficiency required in blue phosphorescent light-emitting elements is underdeveloped so that blue fluorescent light-emitting elements rather than blue phosphorescent light-emitting elements have predominantly been employed in products thus far.

Studies for improving properties of organic electroluminescent elements have reported that the prevention of holes from diffusing into an electron transport layer contributes to the stability of elements. Materials such as BCP or BPhen have been suggested as a blocking material introduced between a light emission layer and an electron transport layer to increase the recombination rate of holes and electrons by preventing the diffusion of holes into the electron transport layer and by limiting holes within the light emission layer. However, being poor in oxidation stability and thermal durability, the derivatives such as BCP or BPhen were observed to reduce the lifespan of organic electroluminescent elements, and thus finally failed in commercialization. Further, such materials inhibit the movement of electrons to increase the driving voltage of the organic electroluminescent element.

DISCLOSURE

Technical Problem

In order to solve the problems encountered in related art, a purpose of the present invention is to provide an organic electroluminescent element outstanding in terms of driving voltage, emission efficiency, and lifespan.

Technical Solution

In order to accomplish the above purpose thereof, the present invention provides an organic electroluminescent element comprising: an anode; a cathode; and an organic layer interposed therebetween, wherein the organic layer comprises a compound represented by the following Formula 1:

[Formula 1]

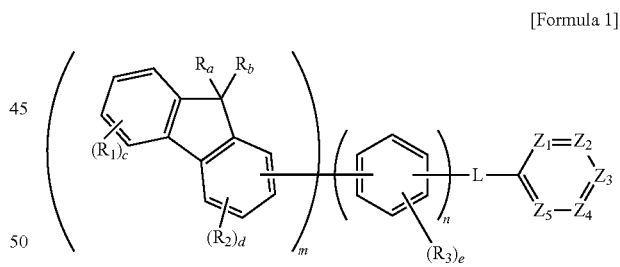

wherein, $R_a$ and $R_b$ are the same or different from each other and are each independently selected from the group consisting of a $C_1$-$C_{40}$ alkyl group and a $C_6$-$C_{60}$ aryl group, or combine with each other to form a fused ring, $R_1$ to $R_3$ are the same or different from each other and are each independently selected from the group consisting of a hydrogen, a deuterium, a halogen, a cyano group, a nitro group, an amino group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nuclear atoms, a $C_6$-$C_{60}$ aryl group, a heteroaryl group having 5 to 60 nuclear atoms, a $C_1$-$C_{40}$ alkyloxy group, a $C_6$-$C_{60}$ aryloxy group, a $C_1$-$C_{40}$ alkylsilyl group, a $C_6$-$C_{60}$ arylsilyl group, a $C_1$-$C_{40}$ alkylboron group, a $C_6$-$C_{60}$ arylboron group, a $C_1$-$C_{40}$ phosphine group, a $C_1$-$C_{40}$ phosphine oxide group, and a $C_6$-$C_{60}$ arylamine group, or each of $R_1$ to $R_3$ forms a fused ring when combined with an adjacent one, L is selected from the group consisting of a single bond, a $C_6$-$C_{18}$ arylene group, and a heteroarylene group having 5 to 18 nuclear atoms, $Z_1$ to $Z_5$ are the same or different from each other and are each independently N or C($R_4$), provided that at least one of $Z_1$ to $Z_5$ is N, and when C($R_4$) is present in a plural number, they are the same or different from each other, c and e are each an integer of 0 to 4, d is an integer of 0 to 3, m and n are each an integer of 1 to 3, $R_4$ is selected from the group consisting of a hydrogen, a deuterium, a halogen, a cyano group, a nitro group, an amino group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nuclear atoms, a $C_6$-$C_{60}$ aryl group, a heteroaryl group having 5 to 60 nuclear atoms, a $C_1$-$C_{40}$ alkyloxy group, a $C_6$-$C_{60}$ aryloxy group, a $C_1$-$C_{40}$ alkylsilyl group, a $C_6$-$C_{60}$ arylsilyl group, a $C_1$-$C_{40}$ alkylboron group, a $C_6$-$C_{60}$ arylboron group, a $C_1$-$C_{40}$ phosphine group, a $C_1$-$C_{40}$ phosphine oxide group and a $C_6$-$C_{60}$ arylamine group, or bonded to an adjacent substituent to form a fused ring, the alkyl and aryl groups of $R_a$ and $R_b$, the alkyl, alkenyl, alkynyl, cycloalkyl, heterocycloalkyl, aryl, heteroaryl, alkyloxy, aryloxy, alkylsilyl, arylsilyl, alkylboron, arylboron, phosphine, phosphine oxide, and arylamine groups of $R_1$ to $R_4$, and the arylene and heteroarylene groups of L may be each independently unsubstituted or substituted with at least one substituent selected from the group consisting of a deuterium, a halogen, a cyano group, a nitro group, an amino group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nuclear atoms, a $C_6$-$C_{60}$ aryl group, a heteroaryl group having 5 to 60 nuclear atoms, a $C_1$-$C_{40}$ alkyloxy group, a $C_6$-$C_{60}$ aryloxy group, a $C_1$-$C_{40}$ alkylsilyl group, a $C_6$-$C_{60}$ arylsilyl group, a $C_1$-$C_{40}$ alkylboron group, a $C_6$-$C_{60}$ arylboron group, a $C_1$-$C_{40}$ phosphine group, a $C_1$-$C_{40}$ phosphine oxide group, and a $C_6$-$C_{60}$ arylamine group, provided that when the substituent is present in a plural number, they are the same or different from each other.

The compound represented by Formula 1 may be contained in a lifetime enhancement layer of the organic layer.

Advantageous Effects

As a lifetime enhancement layer, an electron transport layer, or an electron injection layer all of which comprises a compound having specific physical properties is introduced thereinto, an organic electroluminescent element exhibiting outstanding driving voltage, emission efficiency, and lifespan can be provided.

As the organic electroluminescent element of the present invention is applied thereto, a display panel improved in performance and lifespan can be provided.

BRIEF DESCRIPTION OF THE DRAWINGS

FIG. 1 is a schematic cross-sectional view illustrating an organic electroluminescent element according to one embodiment of the present invention.

MODE FOR INVENTION

Below, a detailed description is given of the present invention.

An embodiment of the present invention provides an organic electroluminescent element, comprising an anode; a cathode; and an organic layer interposed therebetween, wherein the organic layer comprises a compound represented by the following Formula 1:

[Formula 1]

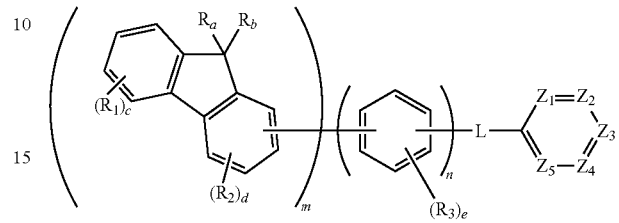

wherein, $R_a$ and $R_b$ are the same or different from each other and are each independently selected from the group consisting of a $C_1$-$C_{40}$ alkyl group and a $C_6$-$C_{60}$ aryl group, or combine with each other to form a fused ring, $R_1$ to $R_3$ are the same or different from each other and are each independently selected from the group consisting of a hydrogen, a deuterium, a halogen, a cyano group, a nitro group, an amino group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nuclear atoms, a $C_6$-$C_{60}$ aryl group, a heteroaryl group having 5 to 60 nuclear atoms, a $C_1$-$C_{40}$ alkyloxy group, a $C_6$-$C_{60}$ aryloxy group, a $C_1$-$C_{40}$ alkylsilyl group, a $C_6$-$C_{60}$ arylsilyl group, a $C_1$-$C_{40}$ alkylboron group, a $C_6$-$C_{60}$ arylboron group, a $C_1$-$C_{40}$ phosphine group, a $C_1$-$C_{40}$ phosphine oxide group, and a $C_6$-$C_{60}$ arylamine group, or each of $R_1$ to $R_3$ forms a fused ring when combined with an adjacent one (in detail, combination between adjacent $R_1$'s, between adjacent $R_2$'s, between adjacent $R_3$'s, or between $R_1$ and $R_2$), L is selected from the group consisting of a single bond, a $C_6$-$C_{18}$ arylene group, and a heteroarylene group having 5 to 18 nuclear atoms, $Z_1$ to $Z_5$ are the same or different from each other and are each independently N or C($R_4$), provided that at least one of $Z_1$ to $Z_5$ is N, and when C($R_4$) is present in a plural number, they are the same or different from each other, c and e are each an integer of 0 to 4, d is an integer of 0 to 3, m and n are each an integer of 1 to 3, $R_4$ is selected from the group consisting of a hydrogen, a deuterium, a halogen, a cyano group, a nitro group, an amino group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nuclear atoms, a $C_6$-$C_{60}$ aryl group, a heteroaryl group having 5 to 60 nuclear atoms, a $C_1$-$C_{40}$ alkyloxy group, a $C_6$-$C_{60}$ aryloxy group, a $C_1$-$C_{40}$ alkylsilyl group, a $C_6$-$C_{60}$ arylsilyl group, a $C_1$-$C_{40}$ alkylboron group, a $C_6$-$C_{60}$ arylboron group, a $C_1$-$C_{40}$ phosphine group, a $C_1$-$C_{40}$ phosphine oxide group and a $C_6$-$C_{60}$ arylamine group, or bonded to an adjacent substituent (in detail, combination between adjacent $R_4$'s) to form a fused ring, the alkyl and aryl groups of $R_a$ and $R_b$, the alkyl, alkenyl, alkynyl, cycloalkyl, heterocycloalkyl, aryl, heteroaryl, alkyloxy, aryloxy, alkylsilyl, arylsilyl, alkylboron, arylboron, phosphine, phosphine oxide, and arylamine groups of $R_1$ to $R_4$, and the arylene and heteroarylene groups of L may be each independently unsubstituted or substituted with at least one substituent selected from the group consisting of a deuterium, a halogen, a cyano group, a nitro group, an amino group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nuclear atoms, a $C_6$-$C_{60}$ aryl group, a heteroaryl group having 5 to 60 nuclear atoms, a $C_1$-$C_{40}$ alkyloxy group, a $C_6$-$C_{60}$ aryloxy group, a $C_1$-$C_{40}$ alkylsilyl group, a $C_6$-$C_{60}$ arylsilyl group, a $C_1$-$C_{40}$ alkylboron group, a $C_6$-$C_{60}$ arylboron group, a $C_1$-$C_{40}$ phosphine group, a $C_1$-$C_{40}$ phosphine oxide group, and a $C_6$-$C_{60}$ arylamine group, provided that when the substituent is present in a plural number, they are the same or different from each other.

FIG. 1 depicts an organic electroluminescent element according to an embodiment of the present invention. According to one embodiment of the present invention, the organic electroluminescent element comprises: an anode 100; a cathode 200; and an organic layer 300 interposed therebetween.

The anode 100 functions to inject holes into the organic layer 300. The material of the anode 100 is not particularly limited, but may be a metal such as vanadium, chromium, copper, zinc, gold, etc.; an alloy thereof; a metal oxide such as zinc oxide, indium oxide, indium tin oxide (ITO), and indium zinc oxide (IZO); a combination of metal and oxide such as ZnO:Al or $SnO_2$:Sb; a conductive polymer such as polythiophene, poly(3-methylthiophene), poly[3,4-(ethylene-1,2-dioxy)thiophene](PEDT), polypyrrole, polyaniline, etc.; and carbon black. No particular limitations are further imparted to the fabrication method of the anode 100, and non-limitative examples include applying an anode material on a substrate made of a silicon wafer, quartz, a glass plate, a metal plate, or a plastic film.

The cathode 200 functions to inject electrons into the organic layer 300. Although no particular limitations are imparted thereto, non-limitative examples of a material available for the cathode include metals such as magnesium, calcium, sodium, potassium, titanium, indium, yttrium, lithium, gadolinium, aluminum, silver, tin, lead, etc; an alloy thereof; and multilayer materials such as LiF/Al, $LiO_2$/Al, etc. Any method that is known in the art may be used for the fabrication of the cathode 200 without particular limitations.

As can be seen in FIG. 1, the organic layer 300 may particularly include at least one selected from the group consisting of a hole injection layer 301, a hole transport layer 302, a light-emitting layer 303, a lifetime enhancement layer 304, an electron transport layer 305, and an electron injection layer 306. In view of the characteristics of organic electroluminescent elements, the organic layer 300 may more particularly include all of the layers.

The hole injection layer 301 and the hole transport layer 302 contribute to the migration of the holes injected from the anode 100 into the light-emitting layer 303. Materials available for the hole injection layer 301 and the hole transport layer 302 are not particularly limited if they have low hole injection barriers and high hole motility, and non-limitative examples thereof include arylamine derivatives.

In the light-emitting layer 303, holes and electrons meet each other to form excitons. According to the material of the light-emitting layer 303, the light emitted by the organic electroluminescent element is determined. The light-emitting layer 303 may contain a host and a dopant, and may particularly contains 70 to 99.9% by weight of host and 0.1 to 30% by weight of dopant. For blue fluorescence, green fluorescence or red fluorescence, the light-emitting layer 303 may particularly contain a host in an amount of 70 to 99.9% by weight and a dopant in an amount of 0.1 to 30% by weight and more particularly a host in an amount of 80 to 99% by weight and a dopant in an amount of 1 to 20% by weight.

No particular limitations are imparted to the host contained in the light-emitting layer 303 if it is known in the art. Non-limitative examples of the host include alkali metal complexes; alkaline earth metal complexes; and fused aromatic ring derivatives. Particularly, preference is made for a host that can increase the emission efficiency and lifespan of the organic electroluminescent element, as exemplified by aluminum complexes, beryllium complexes, anthracene derivatives, pyrene derivatives, triphenylene derivatives, carbazole derivatives, dibenzofuran derivatives, and dibenzothiophene derivatives.

The dopant contained in the light-emitting layer 303 is not particularly limited if it is known in the art, and non-limitative examples thereof include anthracene derivatives, pyrene derivatives, arylamine derivatives, and iridium (Ir)- or platinum (Pt)-containing metal complex compounds.

The light-emitting layer 303 may consist of one layer (monolayer structure) or a plurality of layers (multilayer structure). A multilayer structure of the light-emitting layer 303 may allow the organic electroluminescent element to emit light of various colors. For instance, when a plurality of light-emitting layers is positioned between the hole transport layer 302 and the lifetime enhancement layer 304, an organic electroluminescent element can emit light of a mixed color. In this regard, the light-emitting layers may be made of heterogeneous materials. In addition, a multilayer structure of the light-emitting layer 303, although increasing the driving voltage, makes the current values constant within the organic electroluminescent element, thus improving as much the emission efficiency of the organic electroluminescent element as the number of the light-emitting layers.

As implied in the name thereof, the lifetime enhancement layer 304 aims to improve the lifespan of the organic electroluminescent element, and is provided between the light-emitting layer 303 and the electron transport layer 305. No particular limitations are imparted to a material of the lifetime enhancement layer 304, and a bipolar compound that has both an electron withdrawing group (EWG) with high electron withdrawing ability and an electron donating group (EDG) with high electron donating ability may be preferably used. More particularly, the compound represented by Formula 1 may be used as a material of the lifetime enhancement layer 304.

In detail, the bipolar compound particularly has an ionization potential of 5.5 eV or higher, more particularly 5.5 to 7.0 eV, and most particularly 5.6 to 6.6 eV. Further the bipolar compound particularly has an energy gap between HOMO and LUMO ($E_{HOMO}$-$E_{LUMO}$) of higher than 3.0 eV and more particularly 2.8 to 3.8 eV. In addition, the bipolar compound particularly has a triplet energy of 2.3 eV or higher, more particularly 2.3 to 3.5 eV, and most particularly 2.3 to 3.0 eV. Furthermore, the bipolar compound particularly has a gap between singlet energy and triplet energy of less than 0.7 eV and more particularly 0.01 to 0.7 eV. Given a compound with an ionization potential of 5.5 eV or higher, the lifetime enhancement layer 304 can prevent the diffusion or migration of holes into the electron transport layer 305, thus contributing to improvement in the lifespan of the organic electroluminescent element.

As a rule, holes move depending on ionization potential levels in an organic electroluminescent element. When holes diffuse or move to the electron transport layer 305 through the light-emitting layer 303, irreversible decomposition is generated by oxidation, resulting in a decrease in the lifespan of the organic electroluminescent element. In some embodiments of the present invention, however, the presence of the lifetime enhancement layer 304 that comprises a bipolar compound with an ionization potential of 5.5 eV or higher prevents holes from diffusing or moving to the electron transport layer 305, improving the lifespan of the organic electroluminescent element. That is, holes are blocked by the high energy barrier of the lifetime enhancement layer 304 and thus remain within the light-emitting layer 303.

If the light-emitting layer 303 is made of a red phosphorescent material, an ionization potential of 5.5 eV or higher may be allowed without problems for the bipolar compound contained in the lifetime enhancement layer 304. On the other hand, the use of a green or blue phosphorescent material may particularly require an ionization potential of 6.0 eV or higher for the bipolar compound.

In accordance with some particular embodiments, the bipolar compound has an energy gap between HOMO and LUMO ($E_{HOMO}-E_{LUMO}$) of higher than 3.0 eV, a triplet energy of 2.3 eV or higher, and a gap between singlet energy and triplet energy of less than 0.7 eV. The use of such a compound in the lifetime enhancement layer 304 can prevent the exciton formed in the light-emitting layer 303 from diffusing into the electron transport layer 305 and can interrupt light emission at an interface between the light-emitting layer 303 and the electron transport layer 305. Thanks to the bipolar compound, as a result, the organic electroluminescent element can be prevented from exhibiting spectrum color mixing and can be more stabilized, thus increasing in lifespan.

In one embodiment of the present invention, the bipolar compound bears both an electron withdrawing group (EWG) of high electron withdrawing ability and an electron donating group (EDG) of high electron donating ability, with spatial separation between respective electron clouds of HOMO and LUMO. Due to this, the gap between triplet energy and singlet energy (ΔEst) of the compound is as small as less than 0.7 eV, so that the compound can have high triplet energy (T1) even when the energy gap between HOMO and LUMO ($E_{HOMO}-E_{LUMO}$) exceeds 3.0 eV.

If the light-emitting layer 303 is made of a red phosphorescent material, a triplet energy of 2.3 eV or higher may be allowed without problems for the bipolar compound contained in the lifetime enhancement layer 304. On the other hand, the use of a green or a blue phosphorescent material may particularly require a triplet energy of 2.5 eV or higher and 2.7 eV or higher, respectively, for the bipolar compound.

Both the hole mobility and the electron mobility of the bipolar compound are particularly $1 \times 10^{-6}$ cm²/V·s or higher. The use of the compound in the lifetime enhancement layer 304 prevents the injection of electrons from being delayed compared to the number of the holes injected from the anode 100, thus improving the lifespan of the organic electroluminescent element.

When an electron-hole imbalance occurs as holes and electrons are injected in different numbers from the anode 100 and the cathode 200, respectively, an excess of electrons or holes that has not participated in the formation of excitons through recombination accumulate in the light-emitting layer 303. The electrons or holes accumulated in the light-emitting layer 303 interrupt smooth oxidation and reduction in the light-emitting layer 303 or have a negative influence on adjacent layers, thus reducing the lifespan of the organic electroluminescent element.

In contrast, the bipolar compound contained in the lifetime enhancement layer 304 in accordance with the present invention exhibits a hole motility of $1 \times 10^{-6}$ cm²/V·s or greater at room temperature due to the electron donating group (EDG) and an electron motility of $1 \times 10^{-6}$ cm²/V·s or greater at room temperature due to the electron withdrawing group (EWG). When used in the lifetime enhancement layer 304, such compounds can effectively inject electrons into the light-emitting layer 303. Like this, the smooth injection of electrons into the light-emitting layer 303 increases efficiency in the formation of excitons in the light-emitting layer 303, thus prolonging the lifespan of the organic electroluminescent element.

The bipolar compound particularly has a framework in which a fluorene moiety is bonded to a 6-membered heterocyclic ring through a linker (phenylene, biphenylene or terphenylene). In this context, the bipolar compound may be a compound represented by Formula 1.

According to one embodiment of the present invention, at least one of the lifetime enhancement layer 304, the electron transport layer 305, and the electron injection layer 306 comprises a compound represented by Formula 1.

Further, the compound represented by Formula 1 may be embodied by one of the compounds represented by the following Formulas 2 to 4.

[Formula 2]

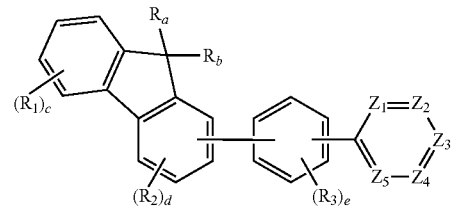

[Formula 3]

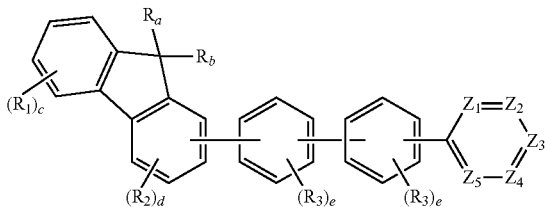

[Formula 4]

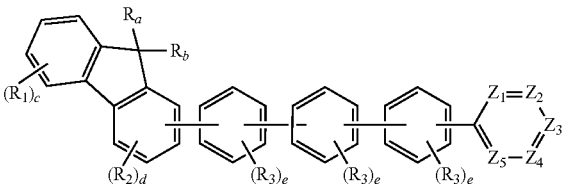

wherein, $R_a$, $R_b$, $R_1$ to $R_3$, $Z_1$ to $Z_5$, c, d, and e are each the same as defined in Formula 1.

In the compound represented by Formula 1 of the present invention, the structure (substituent) represented by

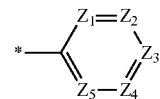

(* is a site where to bond to L) is particularly embodied by one of the structures (substituents) represented by the following C-1 to C-15.

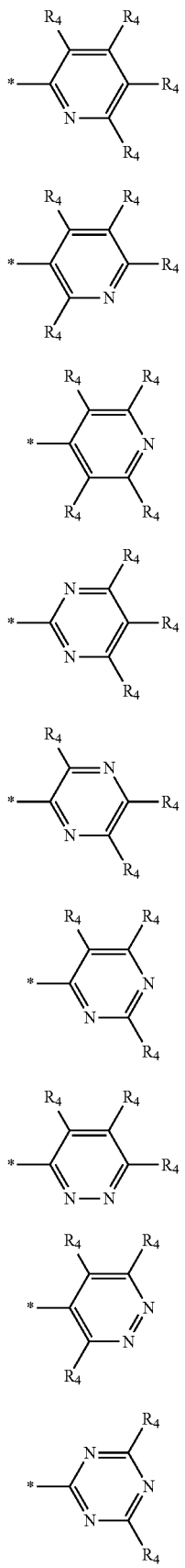
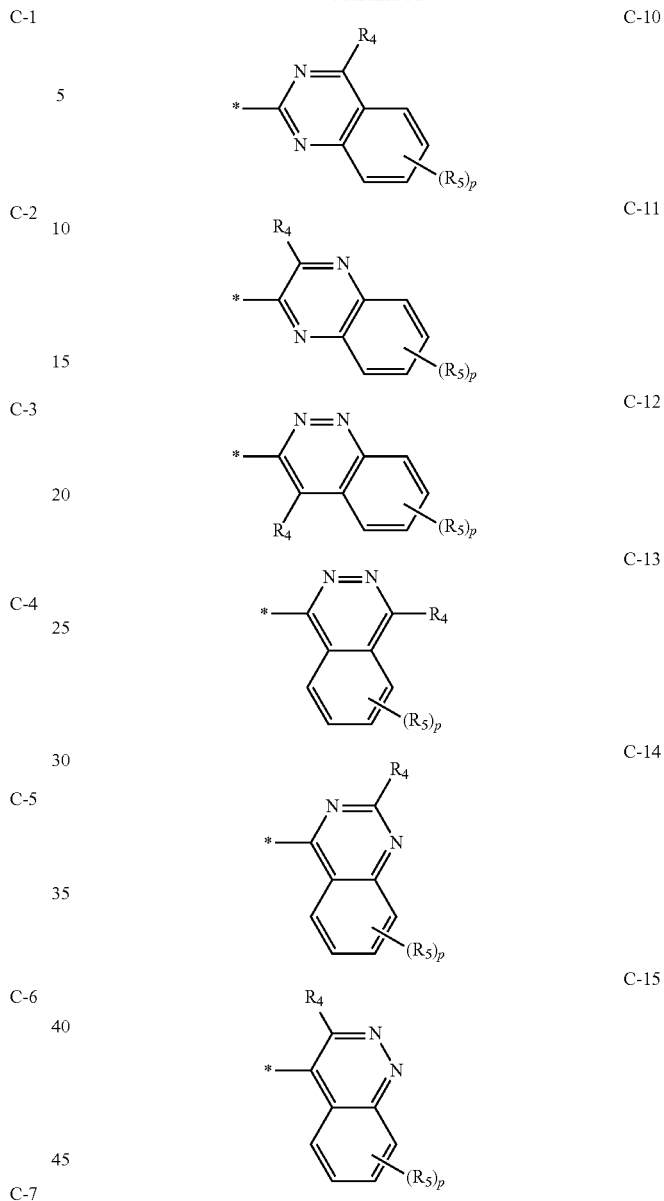

wherein,

R₄ is the same as defined in Formula 1 and plural R₄'s are the same or different from each other, R₅ is selected from the group consisting of a hydrogen, a deuterium, a halogen, a cyano group, a nitro group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nuclear atoms, a $C_6$-$C_{60}$ aryl group, a heteroaryl group having 5 to 60 nuclear atoms, a $C_6$-$C_0$ aryloxy group, a $C_1$-$C_{40}$ alkyloxy group, a $C_6$-$C_{60}$ arylamine group, a $C_1$-$C_{40}$ alkylsilyl group, a $C_1$-$C_{40}$ alkylboron group, a $C_6$-$C_{60}$ arylboron group, a $C_6$-$C_{60}$ arylphosphine group, a $C_6$-$C_{60}$ arylphosphine oxide group, and a $C_6$-$C_{60}$ arylsilyl group, or bonded to an adjacent substituent (in detail, combination between adjacent R5's or between R₄ and R₅) to form a fused ring, p is an integer of 1 to 4, the alkyl, alkenyl, alkynyl, cycloalkyl, heterocycloalkyl, aryl, heteroaryl, aryloxy, alkyloxy, arylamine, alkylsilyl, alkylboron, arylboron, arylphosphine, arylphosphine oxide and arylsilyl groups of $R_5$ may be each independently unsubstituted or substituted with at least one substituent selected from the group consisting of a deuterium, a halogen, a cyano group, a nitro group, a $C_1$-$C_{40}$ alkyl group, a $C_2$-$C_{40}$ alkenyl group, a $C_2$-$C_{40}$ alkynyl group, a $C_6$-$C_{60}$ aryl group, a heteroaryl group having 5 to 60 nuclear atoms, a $C_6$-$C_{60}$ aryloxy group, a $C_1$-$C_{40}$ alkyloxy group, a $C_6$-$C_{60}$ arylamine group, a $C_3$-$C_{40}$ cycloalkyl group, a heterocycloalkyl group having 3 to 40 nuclear atoms, a $C_1$-$C_{40}$ alkylsilyl group, a $C_1$-$C_{40}$ alkylboron group, a $C_6$-$C_{60}$ arylboron group, a $C_6$-$C_{60}$ arylphosphine group, a $C_6$-$C_{60}$ arylphosphine oxide group and a $C_6$-$C_{60}$ arylsilyl group, provided that when the substituent is present in a plural number, they are the same or different from each other.

Here, the structure represented by

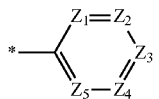

is more particularly the structure represented by C-9. In greater detail, the compound, represented by Formula 1, of the present invention may be those represented by the following Formula 5:

[Formula 5]

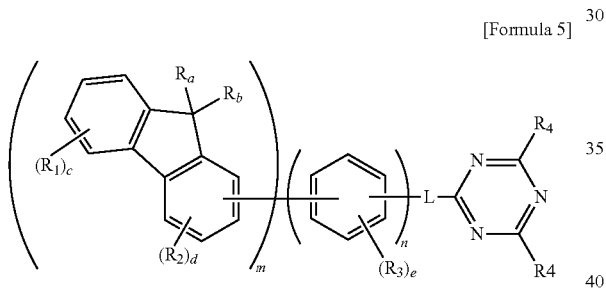

wherein, $R_a$, $R_b$, $R_1$ to $R_4$, L, c, d, e, m, and n are the same each as defined in Formula 1. Here, considering properties of organic electroluminescent elements, $R_4$'s in the compound represented by Formula 5 are particularly the same. That is, identical $R_4$'s particularly give a symmetrical structure to the compound.

When account is taken of properties of organic electroluminescent elements, $R_a$ and $R_b$ in the compound represented Formula 1 of the present invention are each independently a methyl group or a phenyl group, or bond each other to form a fused ring represented by

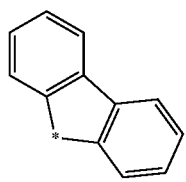 [SMILES: *1c2ccccc2c2ccccc12]

(* is a site where to bond).

In the compound represented by Formula 1, $R_1$ to $R_3$ are each independently selected from the group consisting of a hydrogen, a deuterium, a $C_1$-$C_{40}$ alkyl group, a $C_6$-$C_{60}$ aryl group, a heteroaryl group having 5 to 60 nuclear atoms, and a $C_6$-$C_{60}$ arylamine group. In addition, m and n are each an integer of 1 to 3, and particularly m is 1 and n is 1 or 2.

In the compound represented by Formula 1 of the present invention, L is particularly a single bond, phenylene group, biphenylene group, or terphenylene group. In detail, the linker L is particularly selected from the group consisting of the structures represented by the following L-1 to L-9 (* is a site where to bond).

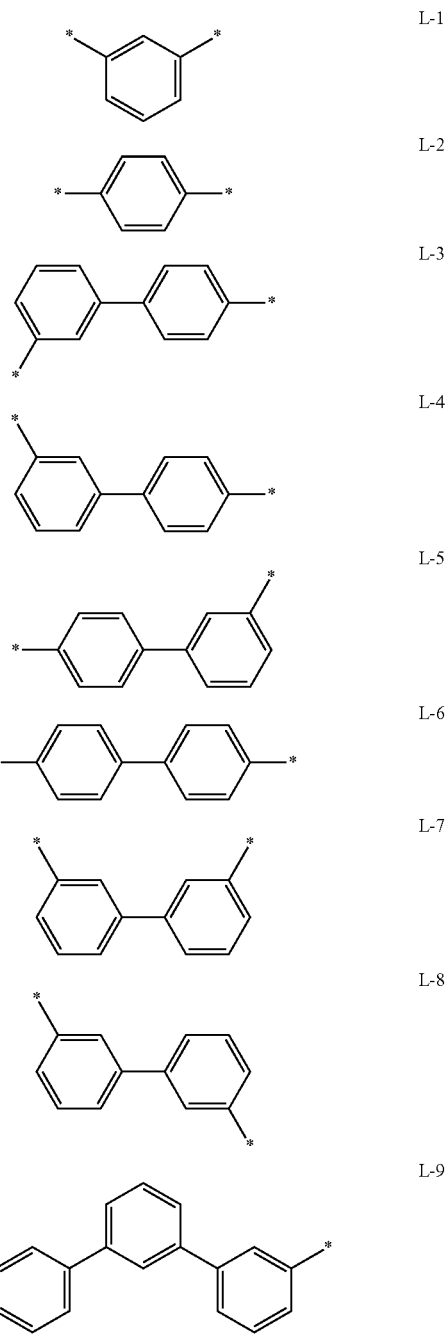

The compounds, represented by Formula 1, of the present invention may be further embodied by the compounds represented by the following Formulas LE-01 to LE-12:

LE-01
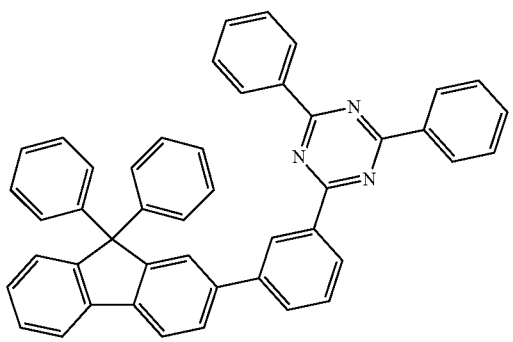
LE-02
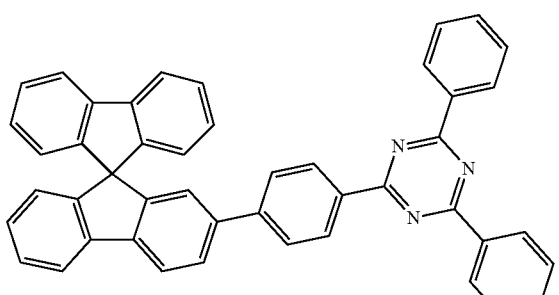
LE-03
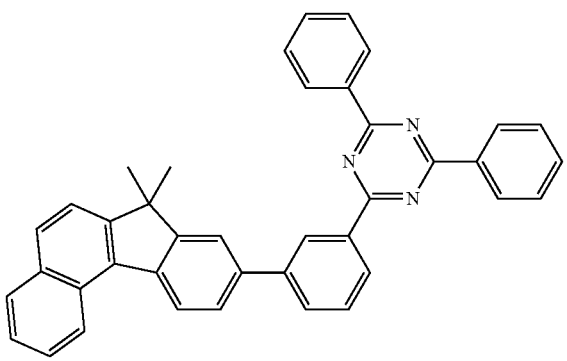
LE-04
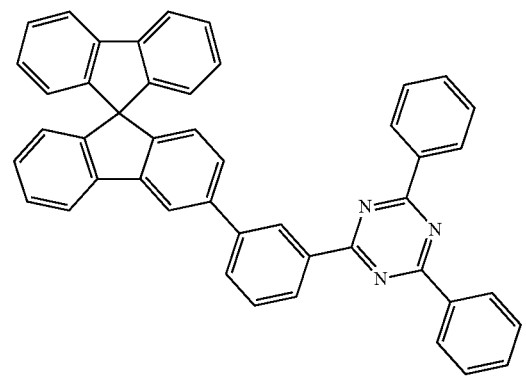
-continued
LE-05
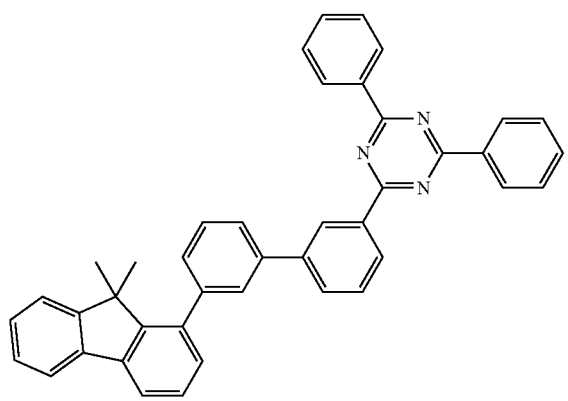
LE-06
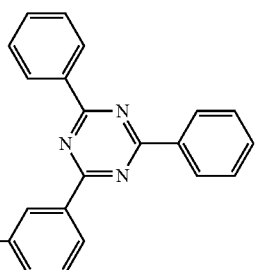
LE-07
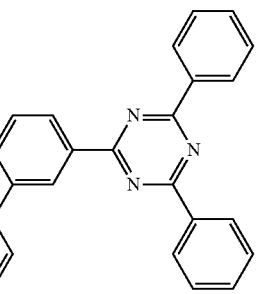
LE-08
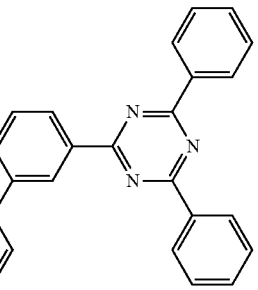

LE-09

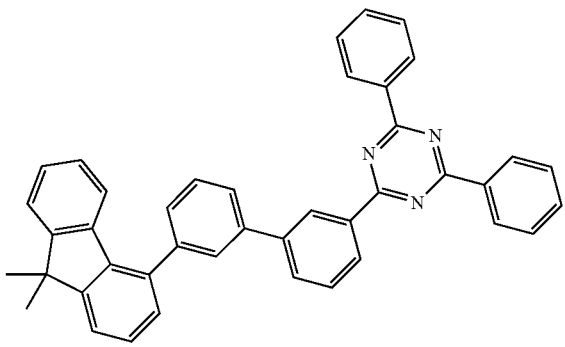

LE-10

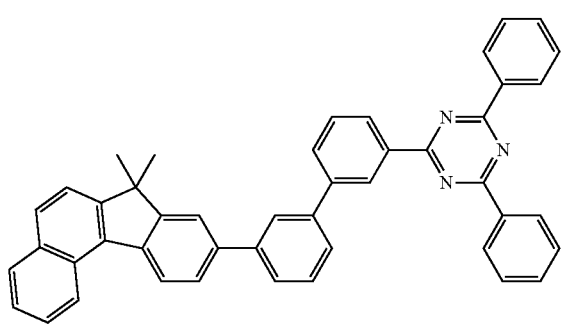

LE-11

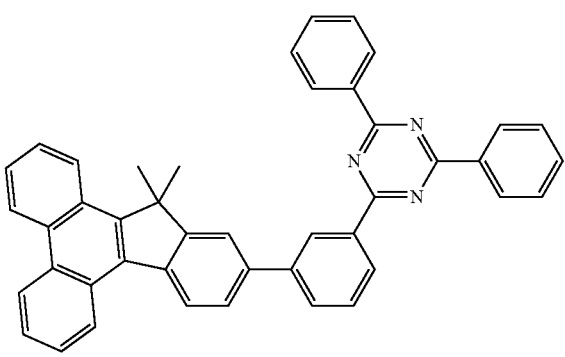

LE-12

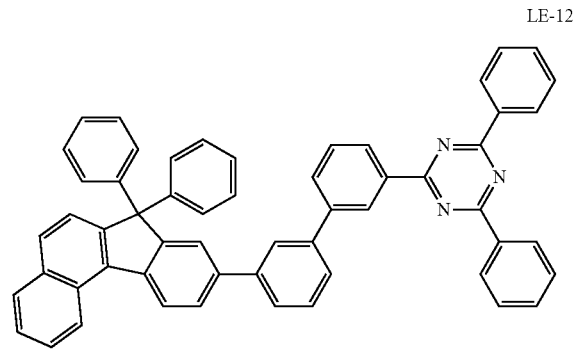

As used herein, the term "alkyl" refers to a monovalent substituent derived from linear or branched saturated hydrocarbon of 1 to 40 carbon atoms. Examples of the alkyl include, but are not limited to, methyl, ethyl, propyl, isobutyl, sec-butyl, pentyl, iso-amyl, hexyl, and the like.

As used herein, the term "alkenyl" refers to a monovalent substituent derived from a linear or branched unsaturated hydrocarbon of 2 to 40 carbon atoms with one or more carbon-carbon double bonds, as exemplified by, but not limited to, vinyl, allyl, isopropenyl, 2-butenyl, and the like.

As used herein, the term "alkynyl" refers to a monovalent substituent derived from a linear or branched unsaturated hydrocarbon of 2 to 40 carbon atoms with at least one carbon-carbon triple bond, as exemplified by, but not limited to, ethynyl, 2-propynyl, and the like.

As used herein, the term "aryl" denotes a monovalent substituent derived from an aromatic hydrocarbon of 6 to 60 carbon atoms with a single ring or a combination of two or more rings in which two or more rings may simply be pendant to each other or fused together. Examples of the aryl include, but are not limited to, phenyl, naphthyl, phenantryl, anthryl, etc.

As used herein, the term "heteroaryl" denotes a monovalent substituent derived from a mono- or polyheterocyclic aromatic hydrocarbon of 5 to 60 nuclear atoms in which at least one, particularly one to three carbon atoms of the ring are substituted by a heteroatom such as N, O, S, or Se. Two or more rings of the heteroaryl, if present, may simply be pendant to each other or fused together or to an aryl group. Examples of heteroaryl include 6-membered monocyclic rings such as pyridyl, pyrazinyl, pyrimidinyl, pyridazinyl, and triazinyl; polycyclic rings such as phenoxathienyl, indolizinyl, indolyl, purinyl, quinolyl, benzothiazole, and carbazolyl; 2-furanyl; N-imidazolyl; 2-ixosazolyl; 2-pyridinyl; and 2-pyrimidinyl, but are not limited thereto.

As used herein, the term "aryloxy" refers to a monovalent substituent represented by RO— wherein R denotes an aryl of 6 to 60 carbon atoms, as exemplified by, but not limited to, phenyloxy, naphthyloxy, diphenyloxy, etc.

As used herein, the term "alkyloxy" refers to a monovalent substituent represented by R'O— wherein R' means an alkyl of 1 to 40 carbon atoms and is construed to include a linear, branched or cyclic structure and examples of which include, but are not limited to, methoxy, ethoxy, n-propoxy, 1-propoxy, t-butoxy, n-butoxy, pentoxy, etc.

As used herein, the term "arylamine" refers to an amine group substituted with an aryl of 6 to 60 carbon atoms.

As used herein, the term "cycloalkyl" refers to a monovalent substituent derived from a mono- or polycyclic non-aromatic hydrocarbon of 3 to 40 carbon atoms, examples of which include cyclopropyl, cyclopentyl, cyclohexyl, norbornyl, and adamantyl, but are not limited thereto.

As used herein, the term "heterocycloalkyl" refers to a monovalent substituent derived from a non-aromatic hydrocarbon of 3 to 40 nuclear atoms in which at least one, particularly one to three carbon atoms of the ring are substituted by a heteroatom such as N, O, S or Se and examples of which include morpholinyl, piperazinyl, and the like, but are not limited thereto.

As used herein, the term "alkylsilyl" refers to a silyl group substituted with an alkyl of 1 to 40 carbon atoms, and the term "arylsilyl" refers to a silyl group substituted with an aryl of 5 to 60 carbon atoms.

As used herein, the term "fused ring" refers to a fused aliphatic ring, a fused aromatic ring, a fused heteroaliphatic ring, a heteroaromatic ring, or a combination thereof.

The compound represented by Formula 1 of the present invention can be synthesized in various manners with reference to the synthesis procedures of the following Examples.

The electron transport layer 305 and the electron injection layer 306 act to migrate electrons injected from cathode 200 into the light-emitting layer 303. A material for the electron transport layer 305 or the electron injection layer 306 is nor particularly limited if it readily allows electron injection and is of large electron motility. Non-limitative examples of the material include compounds represented by Formula 1, anthracene derivatives, heteroaromatic compounds, and alkali metal complexes.

In detail, the electron transport layer 305 and/or the electron injection layer 306 is particularly made of the same material as the lifetime enhancement layer 304, that is, a compound represented by Formula 1. In addition, the electron transport layer 305 and/or the electron injection layer 306 may be co-deposited with alkali metal complexes so as to facilitate the injection of electrons from the cathode. The alkali metal complexes may be based on alkali metals, alkaline earth metals, or rare earth metals.

The organic layer according to one embodiment of the present invention may further comprise an organic film layer (not shown), disposed between the hole transport layer 302 and the light emitting layer 303, for blocking electrons and excitons. The organic film layer is provided with a high LUMO value so as to block the migration of electrons into the hole transport layer 302 and with high triplet energy so as to prevent the excitons of the light-emitting layer 303 into the hole transport layer 302. No particular limitations are imparted to the material for the organic film layer, and non-limitative examples of the material include carbazole derivatives and arylamine derivatives.

The preparation method of the organic layer 300 according to one embodiment of the present invention is not particularly limited, and may be a vacuum evaporation method or a solution coating method as a non-limitative example. Examples of the solution coating method include spin coating, dip coating, doctor blading, inkjet printing, and a thermal transfer method.

The organic electroluminescent element according to some embodiments of the present invention has a structure in which the anode 100, an organic layer 300, and a cathode 200 are sequentially deposited, and may further comprise an insulating layer or an adhesive layer between the anode 100 and the organic layer 300 or between the cathode 200 and the organic layer 300. When a voltage and current is applied thereto, the organic electroluminescent element can prolong the time taken for initial luminance to decrease half (life time) while maintaining the maximum emission efficiency, so that the organic electroluminescent element exhibits excellent lifespan properties.

The present invention will be in greater detail described through the following examples that are set forth to illustrate, but are not to be construed as limiting the present invention.

Preparation Examples 1 to 12: Preparation of Compounds LE-01 to LE-12

Compounds represented by the following LE-01 to LE-12 were prepared as bipolar compounds useful in the present invention and were measured for ΔEst, triplet energy, ionization potential, $E_{HOMO}-E_{LUMO}$, electron motility, and hole motility, using methods known in the art, and the results are summarized in Table 1, below.

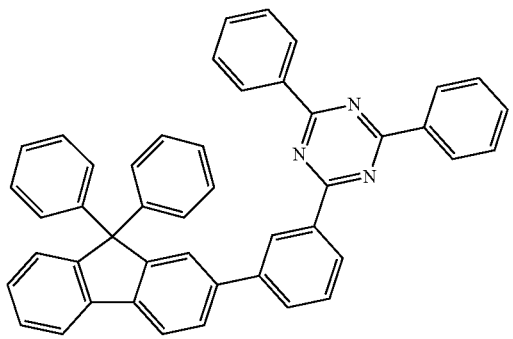

LE-01

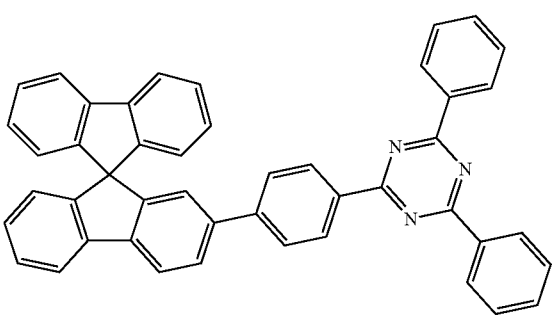

LE-02

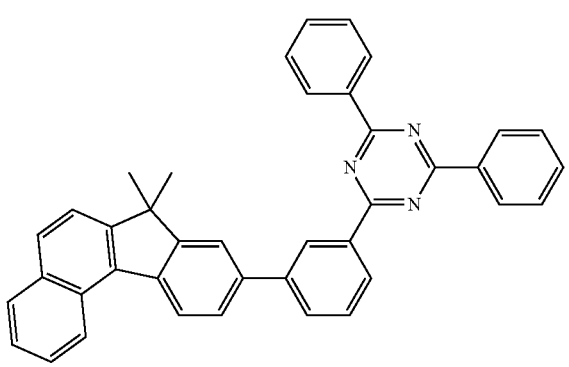

LE-03

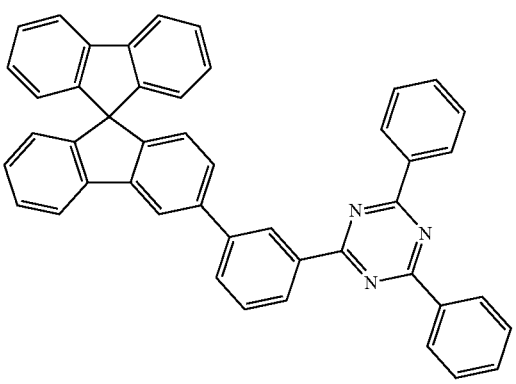

LE-04

LE-05
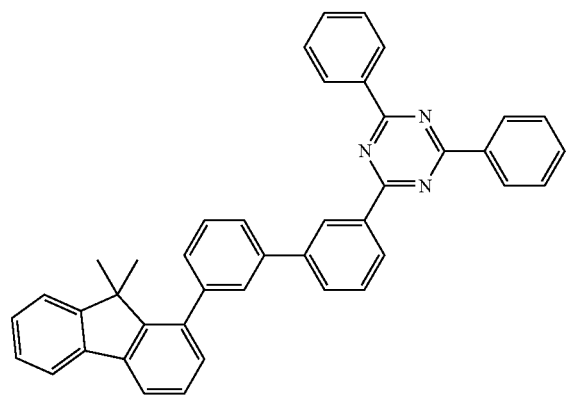
LE-06
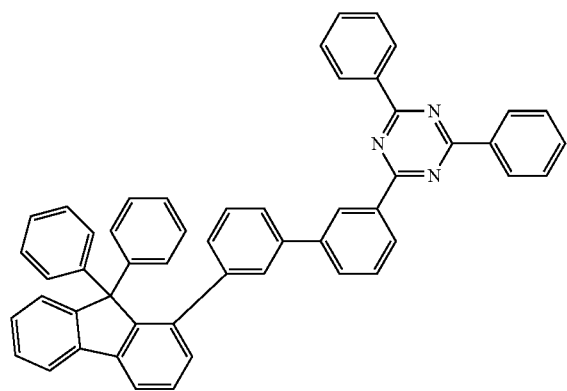
LE-07
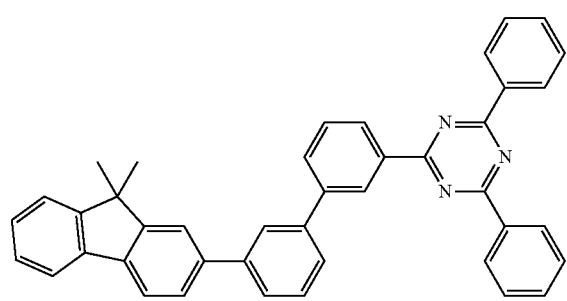
LE-08
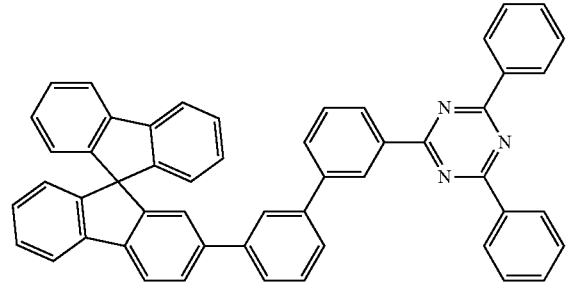
LE-09
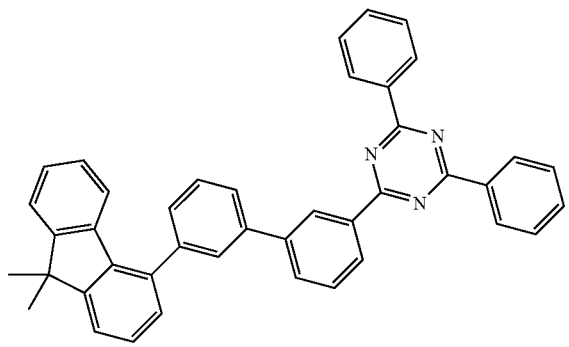
LE-10
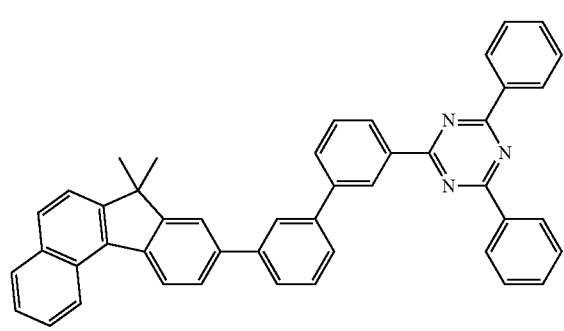
LE-11
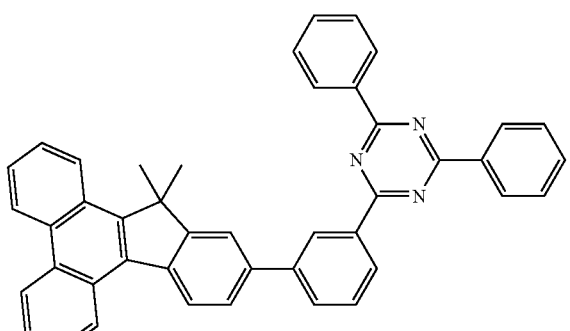
LE-12
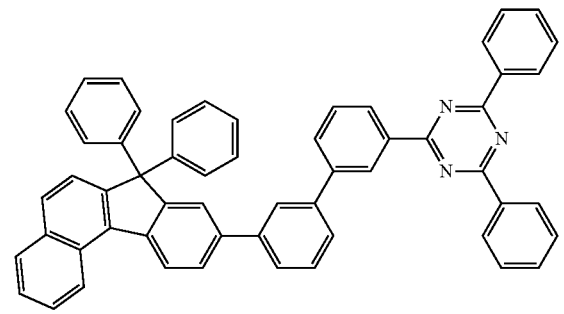

TABLE 1

| Cpd. | Calculated (B3LYP/6-31G*) ΔEst (S1 - T1) | Triplet energy | Measured Ionization potential | $E_{HOMO} - E_{LUMO}$ | Electron motility | Hole motility |
|---|---|---|---|---|---|---|
| LE-01 | 0.42 | 2.78 | 5.92 | 3.49 | $6.8 \times 10^{-4}$ | $7.3 \times 10^{-5}$ |
| LE-02 | 0.52 | 2.68 | 5.88 | 3.45 | $7.3 \times 10^{-4}$ | $5.9 \times 10^{-5}$ |
| LE-03 | 0.47 | 2.71 | 5.93 | 3.56 | $8.1 \times 10^{-4}$ | $7.6 \times 10^{-5}$ |
| LE-04 | 0.57 | 2.73 | 6.12 | 3.44 | $6.6 \times 10^{-4}$ | $5.8 \times 10^{-5}$ |
| LE-05 | 0.51 | 2.81 | 5.97 | 3.63 | $7.3 \times 10^{-4}$ | $8.3 \times 10^{-5}$ |
| LE-06 | 0.48 | 2.83 | 6.16 | 3.64 | $6.8 \times 10^{-4}$ | $7.6 \times 10^{-5}$ |
| LE-07 | 0.49 | 2.82 | 5.97 | 3.60 | $7.8 \times 10^{-4}$ | $8.1 \times 10^{-5}$ |
| LE-08 | 0.55 | 2.80 | 5.96 | 3.58 | $7.9 \times 10^{-3}$ | $7.8 \times 10^{-5}$ |
| LE-09 | 0.52 | 2.82 | 6.01 | 3.62 | $7.3 \times 10^{-4}$ | $7.7 \times 10^{-5}$ |
| LE-10 | 0.47 | 2.72 | 5.89 | 3.45 | $8.5 \times 10^{-4}$ | $7.4 \times 10^{-5}$ |
| LE-11 | 0.38 | 2.65 | 5.87 | 3.41 | $6.7 \times 10^{-4}$ | $6.8 \times 10^{-5}$ |
| LE-12 | 0.41 | 2.71 | 6.01 | 3.51 | $7.7 \times 10^{-4}$ | $7.6 \times 10^{-5}$ |

*For hole motility and electron motility, a film 1 μm thick, made of the bipolar compound, was measured for the transit time of carriers.

Examples 1 to 12: Fabrication of Blue Fluorescent Organic Light-Emitting Element A glass substrate coated with an ITO (indium tin oxide) thin film 1500 Å thick was cleansed by ultrasonication in distilled water and then in a solvent such as isopropyl alcohol, acetone, methanol, etc. and then dried. The glass substrate was transferred to a UV OZONE cleaner (Power sonic 405, Hwashin Tech) and cleaned for 5 min using UV, and transferred to a vacuum evaporator.

On the transparent ITO electrode (substrate) thus obtained, a hole injection layer, a hole transport layer, a light-emitting layer, a lifetime enhancement layer, an electron transport layer, an electron injection layer, and a cathode were deposited in that order to fabricate organic electroluminescent elements. Structures of the fabricated elements are as shown in Table 2, below.

TABLE 2

| | Hole injection layer | Hole transport layer | Light-emitting layer | Lifetime Enhancement Layer | Electron transport layer | Cathode |
|---|---|---|---|---|---|---|
| Cpd. | DS-205 (Doosan Corporation) | NPB | AND +5% DS-405 (Doosan Corporation) | LE-01 to LE-12 | $Alq_3$ | Al |
| Thick. | 80 nm | 15 nm | 30 nm | 5 nm | 25 nm | 200 nm |

The structures of NPB, AND, and $Alq_3$ listed in Table 2 are as follows.

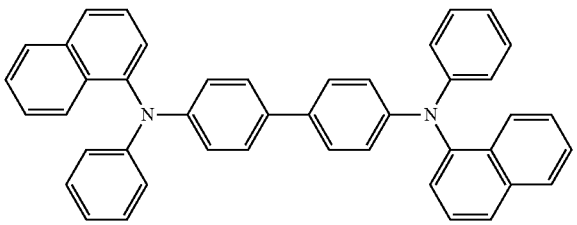

NPB

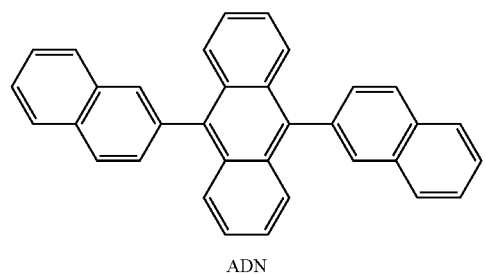

ADN

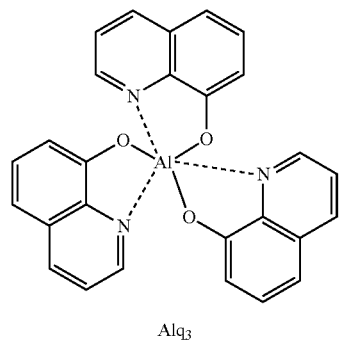

$Alq_3$

Comparative Example 1: Fabrication of Blue Fluorescent Organic Light-Emitting Element An element was fabricated in the same manner as in Example 1, with the exception that an electron transport layer 30 nm thick was vapor deposited without employing a lifetime enhancement layer.

Comparative Example 2: Fabrication of Blue Fluorescent Organic Light-Emitting Element An element was fabricated in the same manner as in Example 1, with the exception of using the following BCP instead of LE-01.

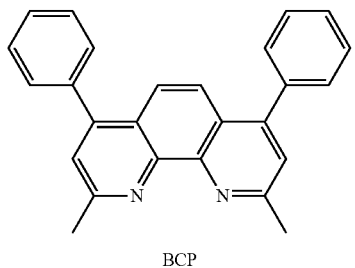

BCP

Experimental Example 1

The elements fabricated in Examples 1 to 12 and Comparative Examples 1 and 2 were measured for driving voltage at a current density of 10 mA/cm$^2$, current efficiency, emitting peak, and lifetime ($T_{97}$), and the results are summarized in Table 3, below.

TABLE 3

| | Cpd. | Driving Volt. (V) | Current Efficiency (cd/A) | Emitting Peak (nm) | Lifespan (hr, $T_{97}$) |
|---|---|---|---|---|---|
| Example 1 | LE-01 | 4.3 | 7.1 | 458 | 63 |
| Example 2 | LE-02 | 4.2 | 6.9 | 458 | 59 |
| Example 3 | LE-03 | 4.6 | 7.0 | 457 | 62 |
| Example 4 | LE-04 | 4.1 | 7.3 | 458 | 58 |
| Example 5 | LE-05 | 4.0 | 8.0 | 458 | 41 |
| Example 6 | LE-06 | 4.2 | 7.9 | 458 | 38 |
| Example 7 | LE-07 | 3.8 | 8.2 | 458 | 42 |
| Example 8 | LE-08 | 3.9 | 8.3 | 457 | 35 |
| Example 9 | LE-09 | 4.1 | 7.8 | 458 | 39 |
| Example 10 | LE-10 | 4.2 | 7.9 | 458 | 64 |
| Example 11 | LE-11 | 4.5 | 7.0 | 458 | 75 |
| Example 12 | LE-12 | 4.3 | 7.4 | 457 | 69 |
| C. Example 1 | — | 4.7 | 5.6 | 458 | 32 |
| C. Example 2 | BCP | 5.3 | 5.9 | 458 | 28 |

*For lifespan, a measurement was made of time taken for luminance to decrease to 97% of the initial value thereof, using a lifetime test system (McScience).

As is understood from the data of Table 3, the organic electroluminescent elements of Examples 1 to 12, each comprising a lifetime enhancement layer in accordance with the present invention, were observed to be superior to those of Comparative Examples 1 and 2 in terms of current efficiency, driving voltage and lifespan.

Examples 13 to 20: Fabrication of Green Phosphorescent Organic Light-Emitting Element A glass substrate coated with an ITO (indium tin oxide) thin film 1500 Å thick was cleansed by ultrasonication in distilled water and then in a solvent such as isopropyl alcohol, acetone, methanol, etc. and then dried. The glass substrate was transferred to a UV OZONE cleaner (Power sonic 405, Hwashin Tech) and cleaned for 5 min using UV, and transferred to a vacuum evaporator.

On the transparent ITO electrode (substrate) thus obtained, a hole injection layer, a hole transport layer, a light-emitting layer, a lifetime enhancement layer, an electron transport layer, an electron injection layer, and a cathode were deposited in that order to fabricate organic electroluminescent elements. Structures of the fabricated elements are as shown in Table 4, below.

TABLE 4

| | Hole injection layer | Hole transport layer | Light-Emitting layer | Lifetime Enhancement Layer | Electron transport layer | Electron injection layer | Cathode |
|---|---|---|---|---|---|---|---|
| Cpd. | m-MTDATA | TCTA | CBP + 10% Ir(ppy)$_3$ | as shown in Table 5, below | Alq$_3$ | LiF | Al |
| Thick. | 60 nm | 80 nm | 30 nm | 5 nm | 25 nm | 1 nm | 200 nm |

The structures of m-MTDATA, TCTA, Ir(ppy)₃, and CBP listed in Table 4 are as follows.

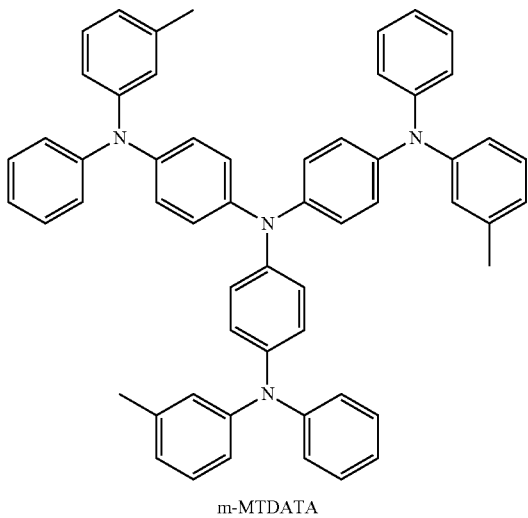

m-MTDATA

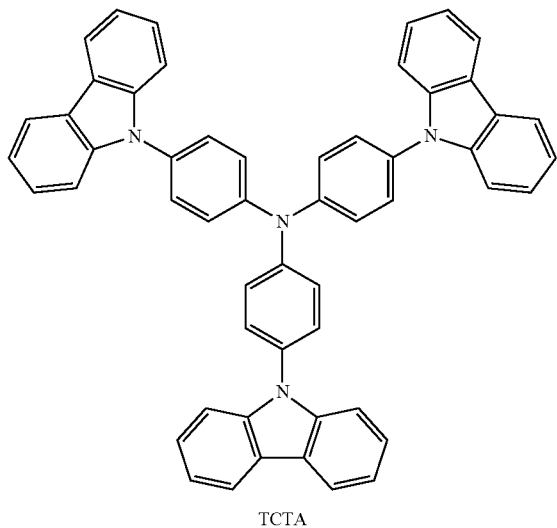

TCTA

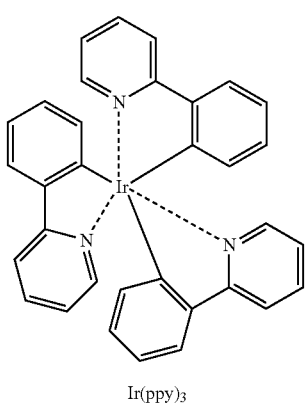

Ir(ppy)₃

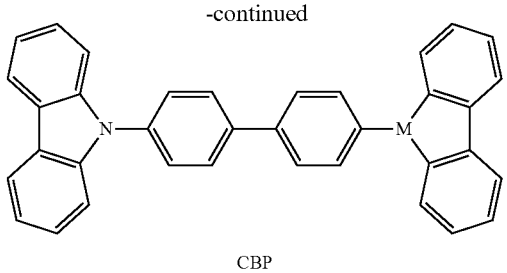

CBP

Comparative Example 3: Fabrication of Green Phosphorescent Organic Light-Emitting Element An element was fabricated in the same manner as in Example 1, with the exception that an electron transport layer 30 nm thick was vapor deposited without employing a lifetime enhancement layer.

Comparative Example 4: Fabrication of Green Phosphorescent Organic Light-Emitting Element An element was fabricated in the same manner as in Example 13, with the exception of using the following BCP instead of LE-01.

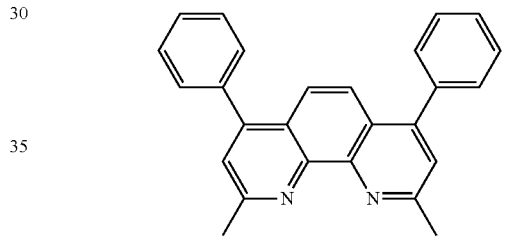

BCP

Experimental Example 2

The elements fabricated in Examples 13 to 20 and Comparative Examples 3 and 4 were measured for driving voltage at a current density of 10 mA/cm², current efficiency, emitting peak, and lifetime ($T_{97}$), and the results are summarized in Table 5, below.

TABLE 5

| | Cpd. | Driving Volt. (V) | Current Efficiency (cd/A) | Emitting Peak (nm) | Lifespan (hr, $T_{97}$) |
|---|---|---|---|---|---|
| Example 13 | LE-01 | 6.4 | 37.0 | 516 | 51 |
| Example 14 | LE-02 | 6.1 | 38.8 | 516 | 53 |
| Example 15 | LE-04 | 6.2 | 38.0 | 516 | 57 |
| Example 16 | LE-05 | 6.4 | 39.0 | 517 | 58 |
| Example 17 | LE-06 | 6.1 | 36.6 | 516 | 69 |
| Example 18 | LE-07 | 6.0 | 41.5 | 515 | 61 |
| Example 19 | LE-08 | 6.4 | 40.6 | 516 | 63 |

TABLE 5-continued

| | Cpd. | Driving Volt. (V) | Current Efficiency (cd/A) | Emitting Peak (nm) | Lifespan (hr, $T_{97}$) |
|---|---|---|---|---|---|
| Example 20 | LE-10 | 6.8 | 37.8 | 516 | 89 |
| C. Example 3 | — | 7.2 | 36.8 | 516 | 45 |
| C. Example 4 | BCP | 7.9 | 40.2 | 516 | 40 |

*For lifespan, a measurement was made of time taken for luminance to decrease to 97% of the initial value thereof, using a lifetime test system (McScience).

As is understood from the data of Table 5, the organic electroluminescent elements of Examples 1 to 12, each comprising a lifetime enhancement layer in accordance with the present invention, were observed to be superior to those of Comparative Examples 1 and 2 in terms of current efficiency, driving voltage and lifespan.

The invention claimed is:

1. An organic electroluminescent element, comprising: an anode; a cathode; and an organic layer interposed therebetween, wherein the organic layer comprises a compound of the following Formula 1:

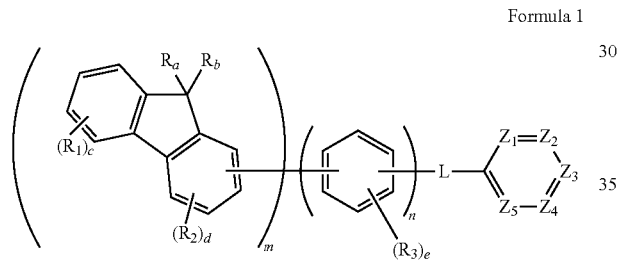

Formula 1 wherein, $R_a$ and $R_b$ are the same or different from each other and are each independently selected from the group consisting of a $C_1$-$C_{40}$ alkyl group and a $C_6$-$C_{60}$ aryl group, or combine with each other to form a fused ring, $R_1$ to $R_3$ are the same or different from each other and are each independently selected from the group consisting of a hydrogen, a deuterium, a halogen, a cyano group, a nitro group, an amino group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nuclear atoms, a $C_6$-$C_{60}$ aryl group, a heteroaryl group having 5 to 60 nuclear atoms, a $C_1$-$C_{40}$ alkyloxy group, a $C_6$-$C_{60}$ aryloxy group, a $C_1$-$C_{40}$ alkylsilyl group, a $C_6$-$C_{60}$ arylsilyl group, a $C_1$-$C_{40}$ alkylboron group, a $C_6$-$C_{60}$ arylboron group, a $C_1$-$C_{40}$ phosphine group, a $C_1$-$C_{40}$ phosphine oxide group, and a $C_6$-$C_{60}$ arylamine group, or each of $R_1$ to $R_3$ forms a fused ring when combined with an adjacent one, L is selected from the group consisting of a single bond, a $C_6$-$C_{18}$ arylene group, and a heteroarylene group having 5 to 18 nuclear atoms, $Z_1$ to $Z_5$ are the same or different from each other and are each independently N or $C(R_4)$, provided that at least one of $Z_1$ to $Z_5$ is N, and when $C(R_4)$ is present in a plural number, they are the same or different from each other, c and e are each an integer of 0 to 4, d is an integer of 0 to 3, m and n are each an integer of 1 to 3, $R_4$ is selected from the group consisting of a hydrogen, a deuterium, a halogen, a cyano group, a nitro group, an amino group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nuclear atoms, a $C_6$-$C_{60}$ aryl group, a heteroaryl group having 5 to 60 nuclear atoms, a $C_1$-$C_{40}$ alkyloxy group, a $C_6$-$C_{60}$ aryloxy group, a $C_1$-$C_{40}$ alkylsilyl group, a $C_6$-$C_{60}$ arylsilyl group, a $C_1$-$C_{40}$ alkylboron group, a $C_6$-$C_{60}$ arylboron group, a $C_1$-$C_{40}$ phosphine group, a $C_1$-$C_{40}$ phosphine oxide group and a $C_6$-$C_{60}$ arylamine group, or bonded to an adjacent substituent to form a fused ring, the alkyl and aryl groups of $R_a$ and $R_b$, the alkyl, alkenyl, alkynyl, cycloalkyl, heterocycloalkyl, aryl, heteroaryl, alkyloxy, aryloxy, alkylsilyl, arylsilyl, alkylboron, arylboron, phosphine, phosphine oxide, and arylamine groups of $R_1$ to $R_4$, and the arylene and heteroarylene groups of L may be each independently unsubstituted or substituted with at least one substituent selected from the group consisting of a deuterium, a halogen, a cyano group, a nitro group, an amino group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nuclear atoms, a $C_6$-$C_{60}$ aryl group, a heteroaryl group having 5 to 60 nuclear atoms, a $C_1$-$C_{40}$ alkyloxy group, a $C_6$-$C_{60}$ aryloxy group, a $C_1$-$C_{40}$ alkylsilyl group, a $C_6$-$C_{60}$ arylsilyl group, a $C_1$-$C_{40}$ alkylboron group, a $C_6$-$C_{60}$ arylboron group, a $C_1$-$C_{40}$ phosphine group, a $C_1$-$C_{40}$ phosphine oxide group, and a $C_6$-$C_{60}$ arylamine group, provided that when the substituent is present in a plural number, they are the same or different from each other.

2. The organic electroluminescent element of claim 1, wherein the organic layer comprises at least one selected form the group consisting of a hole injection layer, a hole transport layer, a light-emitting layer, a lifetime enhancement layer, an electron transport layer, and an electron injection layer, and at least one of the lifetime enhancement layer, the electron transport layer, and the electron injection layer contains the compound of Formula 1.

3. The organic electroluminescent element of claim 2, wherein the lifetime enhancement layer contains the compound of Formula 1.

4. The organic electroluminescent element of claim 3, wherein the light-emitting layer contains a green phosphorescent material and the compound of Formula 1, contained in the lifetime enhancement layer has an ionization potential of 6.0 eV or higher and a triplet energy of 2.5 eV or higher.

5. The organic electroluminescent element of claim 3, wherein the light-emitting layer contains a blue phosphorescent material and the compound of Formula 1, contained in the lifetime enhancement layer has an ionization potential of 6.0 eV or higher and a triplet energy of 2.7 eV or higher.

6. The organic electroluminescent element of claim 2, wherein the electron transport layer contains a compound of Formula 1, the lifetime enhancement layer contains a compound of Formula 1, and the respective compounds contained in the electron transport layer and the lifetime enhancement layer are identical.

7. The organic electroluminescent element of claim 2, wherein the electron injection layer contains a compound of Formula 1,
the lifetime enhancement layer contains a compound of Formula 1, and
the respective compounds contained in the electron injection layer and the lifetime enhancement layer are identical.

8. The organic electroluminescent element of claim 1, wherein the compound of Formula 1 has an ionization potential of 5.5 eV or higher, a gap between HOMO and LUMO of greater than 3.0 eV, a triplet energy of 2.3 eV or higher, and a gap between singlet energy and triplet energy of less than 0.7 eV.

9. The organic electroluminescent element of claim 1, wherein the compound of Formula 1 has a hole motility of $1\times10^{-6}$ cm$^2$/V·s or greater and an electron motility of $1\times10^{-6}$ cm$^2$/V·s or greater at room temperature.

10. The organic electroluminescent element of claim 1, wherein the compound of Formula 1 is selected from the group consisting of respective compounds of the following Formulas 2 to 4:

Formula 2

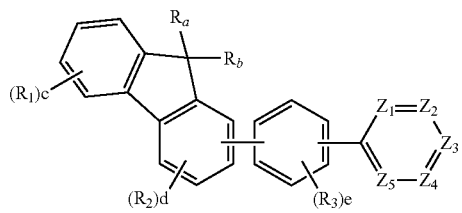

Formula 3

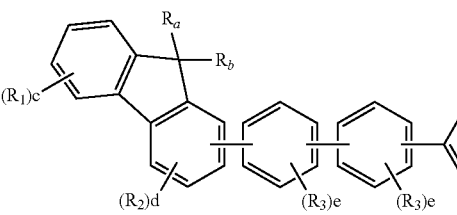

Formula 4

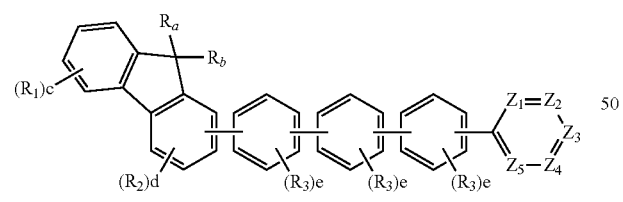

wherein,
$R_a$, $R_b$, $R_1$ to $R_3$, $Z_1$ to $Z_5$, c, d, and e are each the same as defined in claim 1.

11. The organic electroluminescent element of claim 1, wherein the substituent of

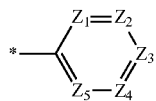

wherein * is a site where to bond with L, in Formula 1 is selected from the group consisting of the structures of the following C-1 to C-15:

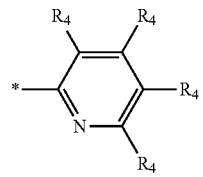
C-1

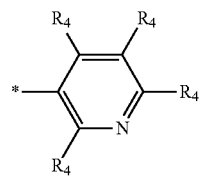
C-2

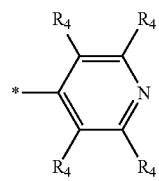
C-3

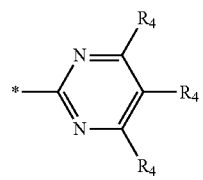
C-4

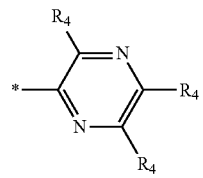
C-5

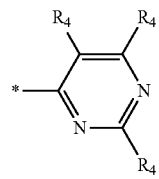
C-6

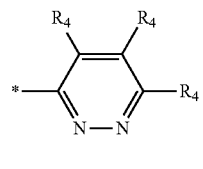
C-7

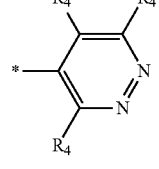
C-8

-continued

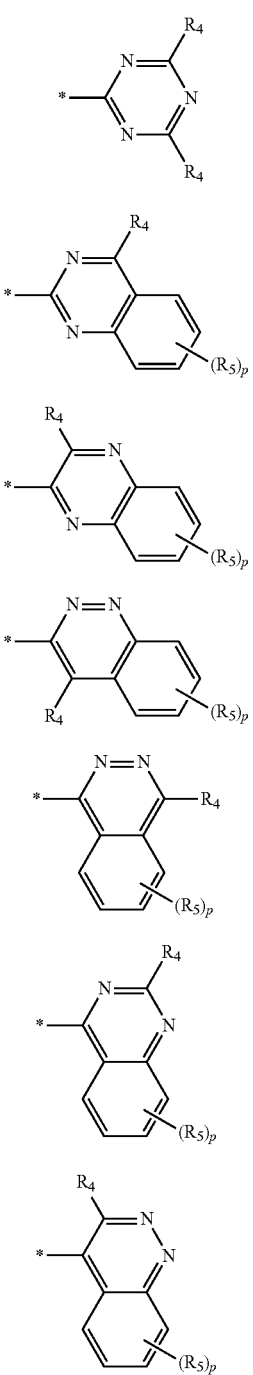

C-9
C-10
C-11
C-12
C-13
C-14
C-15 wherein,
R_4 is the same as defined in claim 1,
R_5 is selected from the group consisting of a hydrogen, a deuterium, a halogen, a cyano group, a nitro group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 nuclear atoms, a $C_6$-$C_{60}$ aryl group, a heteroaryl group having 5 to 60 nuclear atoms, a $C_6$-$C_{60}$ aryloxy group, a $C_1$-$C_{40}$ alkyloxy group, a $C_6$-$C_{60}$ arylamine group, a $C_1$-$C_{40}$ alkylsilyl group, a $C_1$-$C_{40}$ alkylboron group, a $C_6$-$C_{60}$ arylboron group, a $C_6$-$C_{60}$ arylphosphine group, a $C_6$-$C_{60}$ aryl-phosphine oxide group, and a $C_6$-$C_{60}$ arylsilyl group, or bonded to an adjacent substituent to form a fused ring, and
p is an integer of 1 to 4,
the alkyl, alkenyl, alkynyl, cycloalkyl, heterocycloalkyl, aryl, heteroaryl, aryloxy, alkyloxy, arylamine, alkylsilyl, alkylboron, arylboron, arylphosphine, arylphosphine oxide and arylsilyl groups of R_5 may be each independently unsubstituted or substituted with at least one substituent selected from the group consisting of a deuterium, a halogen, a cyano group, a nitro group, a $C_1$-$C_{40}$ alkyl group, a $C_2$-$C_{40}$ alkenyl group, a $C_2$-$C_{40}$ alkynyl group, a $C_6$-$C_{60}$ aryl group, a heteroaryl group having 5 to 60 nuclear atoms, a $C_6$-$C_{60}$ aryloxy group, a $C_1$-$C_{40}$ alkyloxy group, a $C_6$-$C_{60}$ aryl amine group, a $C_3$-$C_{40}$ cycloalkyl group, a heterocycloalkyl group having 3 to 40 nuclear atoms, a $C_1$-$C_{40}$ alkylsilyl group, a $C_1$-$C_{40}$ alkylboron group, a $C_6$-$C_{60}$ arylboron group, a $C_6$-$C_{60}$ arylphosphine group, a $C_6$-$C_{60}$ arylphosphine oxide group, and a $C_6$-$C_{60}$ arylsilyl group, provided that when the substituent is present in a plural number, they are the same or different from each other.

12. The organic electroluminescent element of claim 11, wherein the compound of Formula 1 is a compound of the following Formula 5:

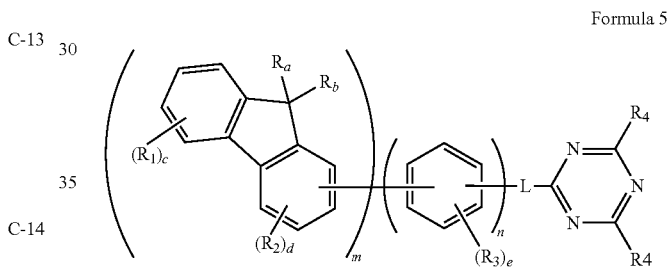

Formula 5 wherein,
$R_a$, $R_b$, $R_1$ to $R_4$, L, c, d, e, m, and n are each the same as defined in claim 1.

13. The organic electroluminescent element of claim 12, wherein R_4's are identical.

14. The organic electroluminescent element of claim 1, wherein $R_a$ and $R_b$ are the same or different from each other and are each independently a methyl group or a phenyl group or bond each other to form a fused ring of

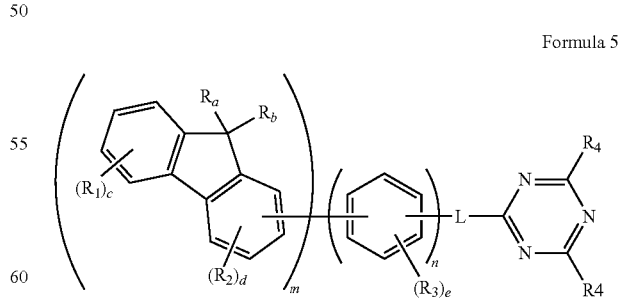

Formula 5 wherein * is a site where to bond.

15. The organic electroluminescent element of claim 1, wherein L is selected from the group consisting of the structures of the following L-1 to L-9, wherein * is a site where to bond:

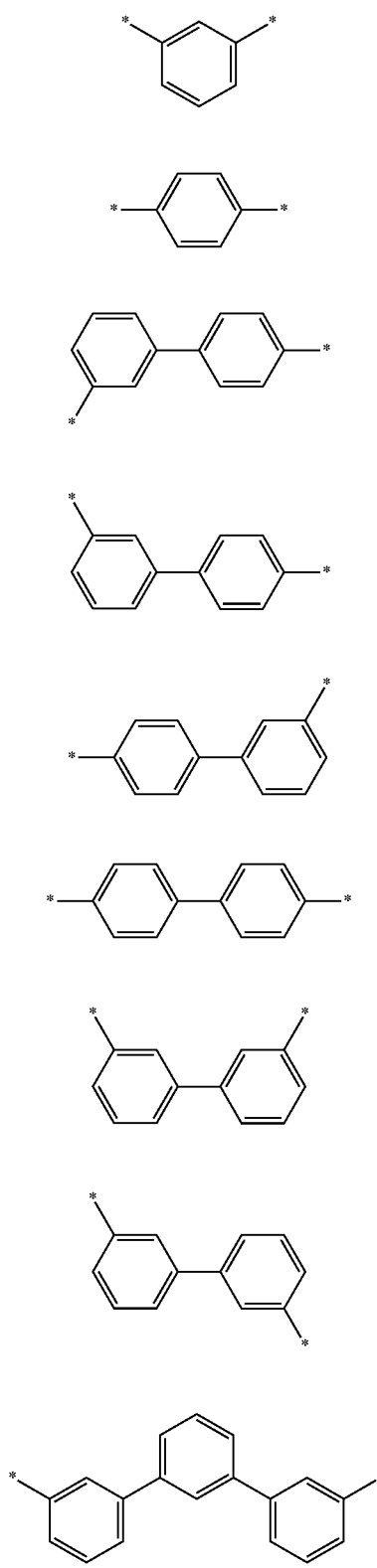
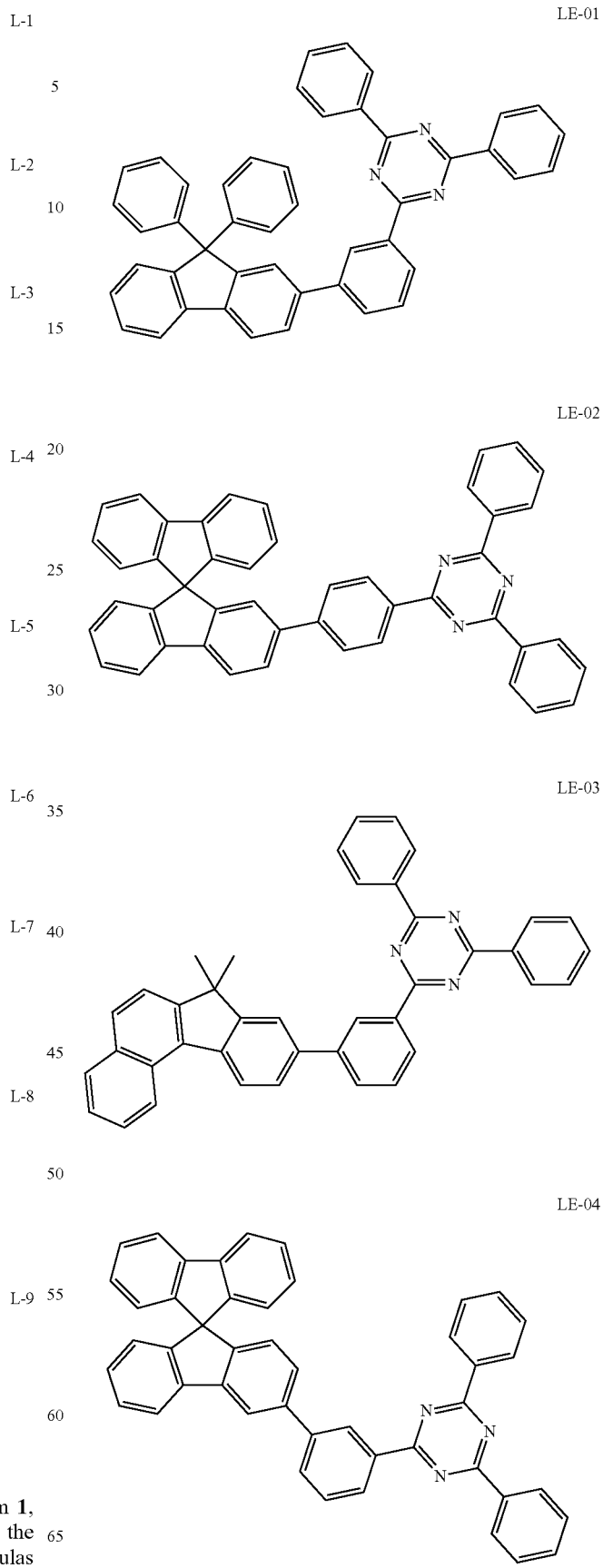
16. The organic electroluminescent element of claim 1, wherein the compound of Formula 1 is selected from the group consisting compounds of the following Formulas LE-01 to LE-12:

LE-05
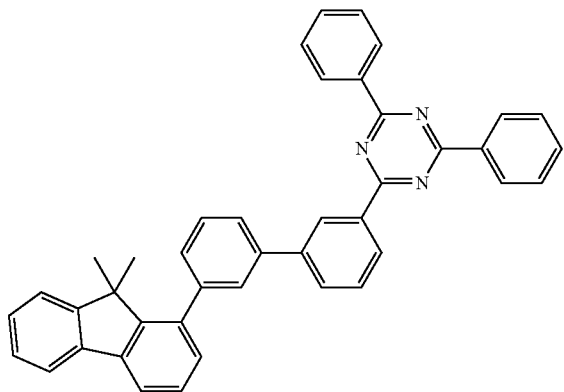
LE-06
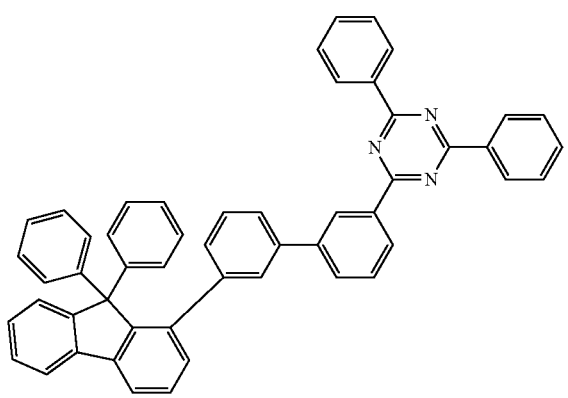
LE-07
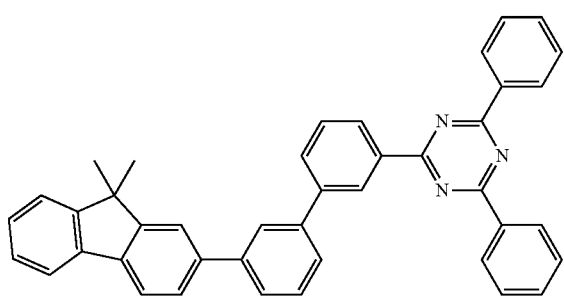
LE-08
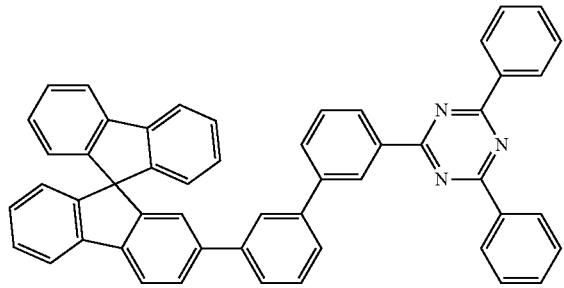
LE-09
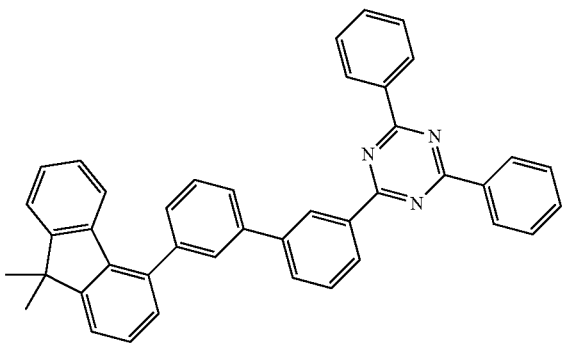
LE-10
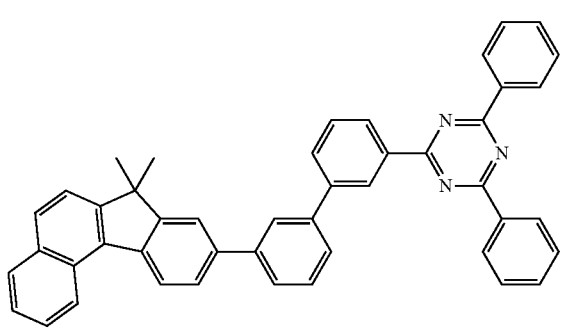
LE-11
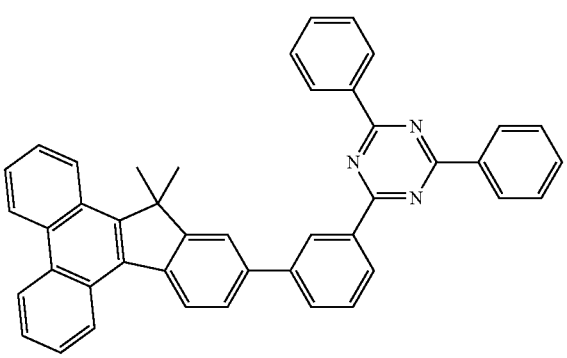
LE-12
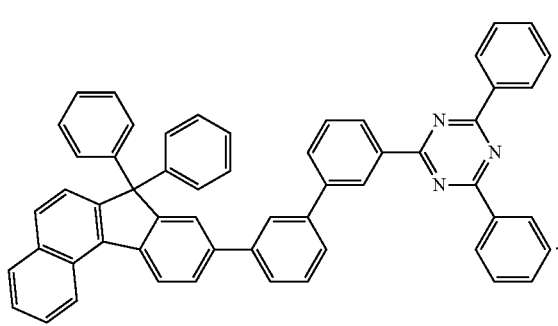
* * * * *